US006045527A

United States Patent [19]
Appelbaum et al.

[11] Patent Number: 6,045,527
[45] Date of Patent: *Apr. 4, 2000

[54] DETECTION OF OPHTHALMIC SURGICAL HANDPIECE USING SHORTING BAR

[75] Inventors: Peter Francis Appelbaum; Kevin Paul Kepley, both of Ballwin, Mo.

[73] Assignee: Bausch & Lomb Surgical, Inc., Claremont, Calif.

[ * ] Notice: This patent issued on a continued prosecution application filed under 37 CFR 1.53(d), and is subject to the twenty year patent term provisions of 35 U.S.C. 154(a)(2).

[21] Appl. No.: 08/916,463

[22] Filed: Aug. 22, 1997

Related U.S. Application Data

[60] Provisional application No. 60/025,498, Aug. 29, 1996.

[51] Int. Cl.[7] .................................................. A61B 17/20
[52] U.S. Cl. ........................ 604/22; 606/107; 200/51.09; 200/51.1
[58] Field of Search .............................. 604/22; 601/2–3; 606/169, 107; 607/97; 200/51 R, 51.09, 51.1

[56] References Cited

U.S. PATENT DOCUMENTS 4,059,739  11/1977  Girismen .
5,151,085  9/1992  Sakurai et al. .
5,425,704  6/1995  Sakurai et al. .

*Primary Examiner*—Mark Bockelman
*Attorney, Agent, or Firm*—Grant D. Kang

[57] ABSTRACT

A system for controlling a plurality of ophthalmic microsurgical instruments connected thereto. The microsurgical instruments are for use by a user such as a surgeon in performing ophthalmic surgical procedures. The system includes a data communications bus and a user interface connected to the data communications bus. The user interface provides information to the user and receives information from the user which is representative of operating parameters of the microsurgical instruments. The system also includes surgical modules connected to and controlling the microsurgical instruments as a function of at least one of the operating parameters. The surgical modules are also connected to the data communications bus. The data communications bus provides communication of data representative of the operating parameters between the user interface and the surgical modules. Other features are also disclosed including a main control, an endo-illuminator system, a phacoemulsification handpiece, surgical scissors, a vitrectomy cutter, a surgical foot control, a remote control, a cart.

4 Claims, 4 Drawing Sheets

Microfiche Appendix Included
(32 Microfiche, 6539 Pages)

DETECTION OF OPHTHALMIC SURGICAL HANDPIECE USING SHORTING BAR

MICROFICHE APPENDIX

This application includes a microfiche appendix of 32 pages and 6,539 frames which is a copy of the provisional application 60/025,498, filed Aug. 29, 1996, under which priority is claimed and updated source code.

BACKGROUND OF THE INVENTION

This invention relates specifically to the field of ophthalmic surgical handpieces. More particularly this embodiment relates to an apparatus and method for detecting the presence of an ophthalmic surgical handpiece which is electrically isolated from ground and the power source.

The use of ultrasonic handpieces or probes for the removal of cataracts from the human eye is well known. Typically, this procedure, called phacoemulsification or phacofragmentation, uses ultrasonic probes for rupturing cataracts in the eye combined with aspiration of the resulting debris. Ultrasonic phacoemulsification probes conventionally include a piezoelectric crystal(s) affixed to the probe body. The crystal is driven by an electric power source and it converts the electric power to ultrasonic power which is applied by the probe to the eye. The amount of power applied by the probe is a function of the frequency and amplitude of the driving electrical waveform and it is typically under control of the surgeon using the probe.

Prior art circuits for phacoemulsification probes have operated in a grounded patient configuration. The prior art circuits have included an apparatus for sensing the presence of the phacoemulsification handpiece or probe, but the handpiece and the sensing apparatus have been connected to ground.

SUMMARY OF THE INVENTION

The present invention includes an ophthalmic surgical handpiece which is isolated from its source of electric power by a first transformer. An apparatus to detect the presence of the handpiece is also provided. The detection apparatus comprises a second transformer which has a resistor connected across its secondary winding and a detection circuit connected to its primary winding. The detection circuit includes a comparator which measures the electrical signal input to determine the presence of the ophthalmic surgical handpiece. When the handpiece is connected, a shorting bar in the handpiece is connected across the secondary winding of the second transformer, changing the signal measured on the primary winding of the transformer. If the handpiece is present, the detection apparatus will provide a signal to the user interface control software program which will activate a relay, such as an electric or electromechanical switch, to connect the electric power source to the ophthalmic surgical handpiece through the first transformer.

The present invention further includes a method for detecting the presence of an ophthalmic surgical handpiece. The method includes the steps of applying an alternating current electric signal to the primary windings of a transformer, receiving a second electric signal determined by the reflected impedance of the load at the secondary windings of the transformer, comparing the second electric signal to a standard to determine the presence of the handpiece. The method may also include the step of activating a switch to provide an electric power source to the detected handpiece.

In another embodiment, the present invention includes an apparatus to detect the presence of an ultrasonic ophthalmic surgical handpiece, preferably a phacoemulsification or phacofragmentation handpiece, which is electrically isolated from its source of electric power by a transformer. The transformer has two primary windings and one secondary winding. The first primary winding is used to provide electric power to the ultrasonic ophthalmic surgical handpiece and the second primary winding is used in the handpiece detection apparatus. The detection apparatus comprises the second primary winding of the transformer and a detection circuit which is connected to the second primary winding and the detection apparatus may include a signal source. The detection circuit includes a high pass filter and a comparator which compares the electrical signal input to a standard to determine the presence of the ultrasonic ophthalmic surgical handpiece. When the handpiece is connected, the reflected impedance at the second primary winding of the transformer will be changed, changing the signal measured by the detection circuit. If the handpiece is present, the detection circuit will provide a signal to the user interface control software program which will activate a relay, such as an electric or electromechanical switch, to connect the electric power source to the handpiece through the first primary winding of the transformer.

The present invention further includes a method for detecting the presence of an ultrasonic ophthalmic surgical handpiece. The method includes the steps of applying an alternating current electric signal to a primary winding of a transformer having a first and a second primary winding and one secondary winding, receiving a second electric signal at the second primary winding determined by the reflected impedance of the load at the secondary winding of the transformer and comparing the second electric signal to a standard to determine the presence of the handpiece. The method may also include the step of activating a switch to connect an electric power source through the first primary winding of the transformer to the detected handpiece.

Use of an isolated ophthalmic surgical handpiece and the isolated apparatus and method for detecting the presence of the handpiece of this invention provides increased patient safety. Further it allows recognized safety standards, such as the voluntary standard IEC601-1 promoted by the International Electrotechnical Commission, Underwriters Laboratory standard UL2601 and the European Union standard EN60601-1, to be met.

DETAILED DESCRIPTION OF THE PREFERRED EMBODIMENT

Figure 1:
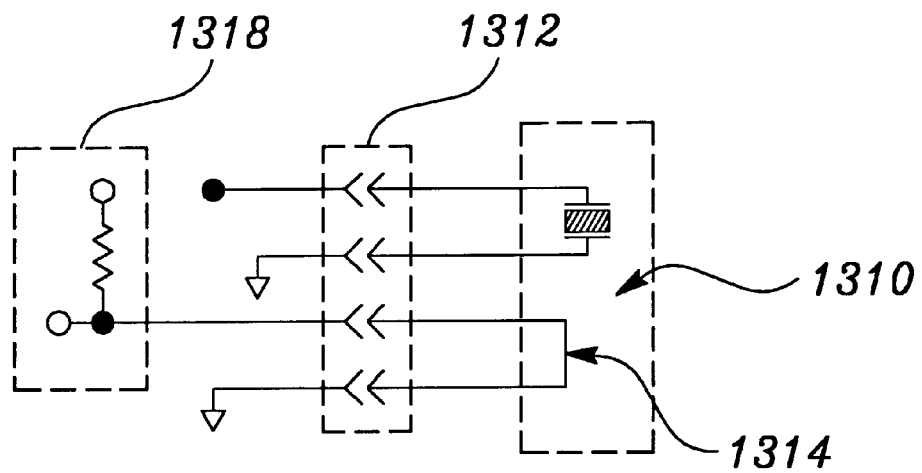
FIG. 1 is an illustration of a prior art circuit to detect the presence of a phacoemulsification handpiece in a grounded patient configuration.

Turning to the drawings, FIG. 1 illustrates a prior art circuit to detect the presence of a phacoemulsification handpiece in a grounded patient configuration. The phacoemulsification handpiece or probe 1310 is connected through connector 1312 directly to the electric power source (not shown). The phacoemulsification handpiece 1310 includes shorting bar 1314 which is connected through different connection points in connector 1312 to the detection circuit 1318. When a phacoemulsification handpiece is detected, the control software allows power to be supplied to the handpiece.

Figure 2:
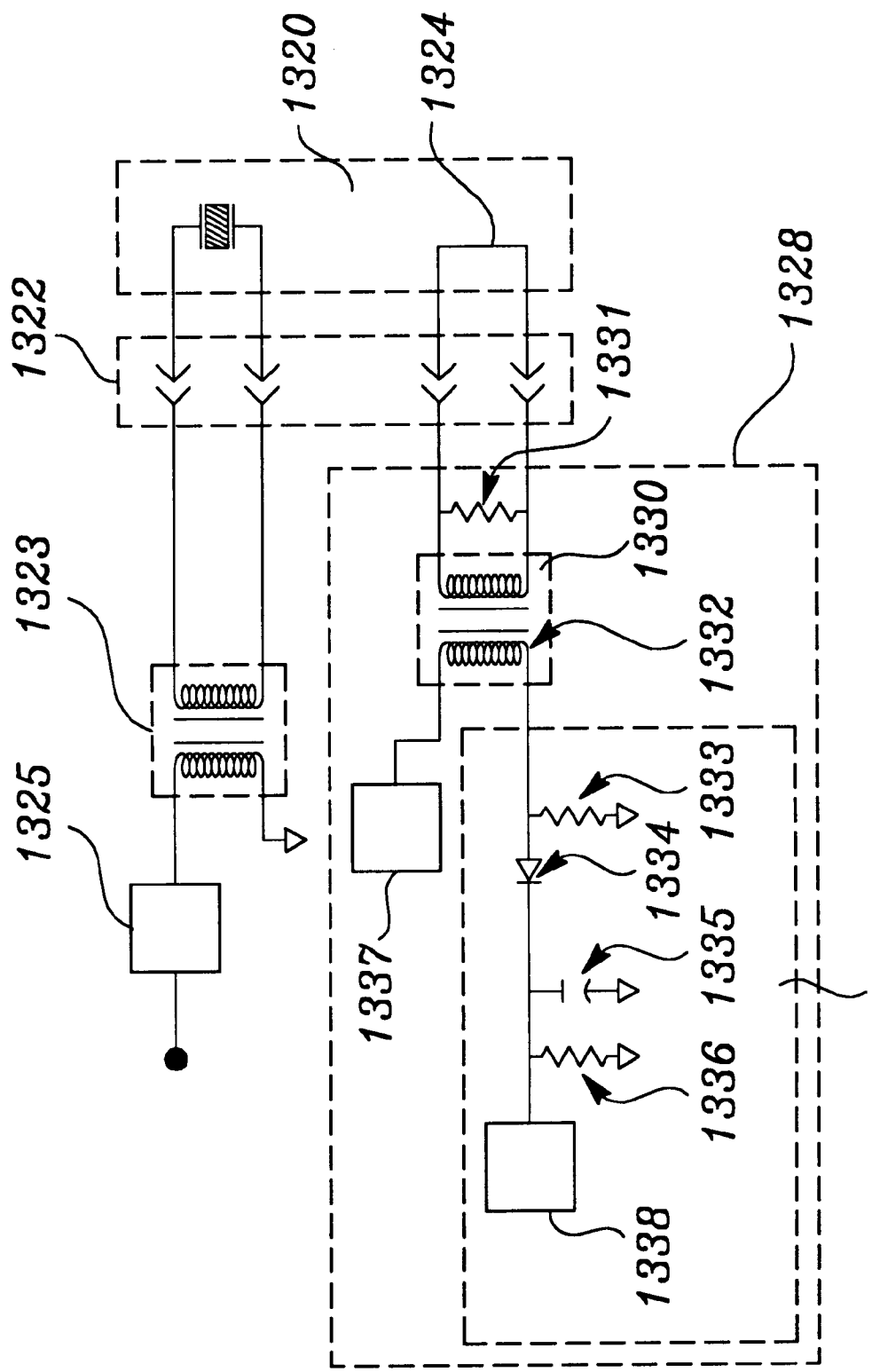
FIG. 2 is an illustration of the isolated phacoemulsification handpiece detection apparatus of the present invention.

FIG. 2 illustrates an embodiment of the present invention, an ophthalmic surgical handpiece detection apparatus which has an electrically isolated, floating patient configuration. An ophthalmic surgical handpiece or probe 1320 is connected through connector 1322 to the secondary windings of first transformer 1323 which provides electric power to the handpiece 1320 while isolating the handpiece 1320 from the electric power source (not shown). The ophthalmic surgical handpiece 1320 is a conventionally known probe such as those produced by Storz Instrument Company and in a preferred embodiment is one of the surgical scissors or the ultrasonic handpieces used for phacoemulsification or phacofragmentation procedures. The first transformer is a conventional power transformer that provides the desired isolation between the handpiece 1320 and the source of electric power. The primary windings of first transformer 1323 are connected to the electric power source (not shown) through apparatus, switch or relay 1325 which is controlled by software activated by a signal from detection apparatus 1328. Relay 1325 may be any conventional electrical or electromechanical switch capable of switching the electrical power required by the handpiece 1320 on and off.

Detection apparatus 1328 includes second transformer 1330 which has resistor 1331 (10 k ohms) connected across its secondary windings and detection circuit 1329 connected to its primary winding. Second transformer 1330 is a conventional transformer having a 1:1 ratio between its primary and secondary windings, although transformers having different ratios may be used. Second transformer 1330 provides isolation between the handpiece 1320 and the handpiece detection circuit 1329. End 1332 of the primary winding of second transformer 1330 is connected to ground through resistor 1333 (1 k ohms). End 1332 is also connected to the anode of diode 1334 (1N918, 1N4148 or similar diode) and resistor 1336 (100 k ohms) and capacitor 1335 (0.01 μfarad) are connected in parallel between the cathode of diode 1334 and ground. An alternating current signal source 1337 provides a signal to the primary winding of second transformer 1330. Comparator 1338, connected to the cathode of diode 1334, compares the signal that it receives with a standard signal to determine the presence of the handpiece 1320 and, when the handpiece is present, the comparator 1338 provides a signal to the user interface control software which will activate relay 1325 to provide electric power to the handpiece 1320. Alternatively comparator 1338 may be connected directly to relay 1325 so that the output signal from comparator 1338 will activate relay 1325. The shorting bar 1324, included in the handpiece 1320, is connected through connector 1322 in parallel with resistor 1331 across the secondary winding of second transformer 1330 when the handpiece 1320 is connected to the circuit. The detection circuit 1329 detects the presence of the handpiece 1320 by the change in voltage measured.

In operation of the detection apparatus 1328, an alternating current signal, such as a 5 volt, 62.5 hertz square wave, is provided to the primary winding of second transformer 1330. When the ophthalmic surgical handpiece 1320 is not connected, the reflected impedance of the load provided by resistor 1331 on the secondary winding side of second transformer 1330 is relatively high and the voltage at the anode of diode 1334 is insufficient to forward bias the diode. Thus, the signal received by the comparator 1338, the signal measured by the detection circuit 1329, is essentially zero indicating that the handpiece 1320 is not connected. When the ophthalmic surgical handpiece 1320 is connected, shorting bar 1324 is connected across the secondary winding of second transformer 1330 and the reflected impedance of the load on the secondary winding of second transformer 1330 is relatively low, resulting in a higher voltage measured by detection circuit 1329. This higher voltage at the anode of diode 1334 is sufficient to forward bias the diode to provide a rectified, filtered signal to comparator 1338 which compares the signal to a standard. If the comparator 1338 determines that a handpiece 1320 is present, the comparator 1338 provides a signal to the user interface controlling software indicating the presence of the handpiece 1320 and the software activates relay 1325, which may be an electric or electro-mechanical switch, to provide electrical power to the handpiece 1320 through first transformer 1323.

It should be recognized that the selected values for the resistors, capacitors and other components and for stated voltages and frequencies are provided for illustration of the invention and not as the only combination and that the values of each may be changed without changing the invention.

The present invention further includes a method for detecting the presence of an ophthalmic surgical handpiece. The method includes the steps of providing an alternating current electric signal to the primary winding of a transformer, receiving a second electric signal determined by the reflected impedance of the load on the secondary winding of the transformer and comparing the second electric signal to a standard to determine the presence of the ophthalmic surgical handpiece. The method may also include the step of activating a switch to connect an electric power source to the detected handpiece.

The electrical isolation provided by transformers 1323 and 1330 allow the controls to sense the presence of the ophthalmic surgical handpiece and to provide power to the handpiece while maintaining the integrity of the isolated patient configuration. This is an important safety consideration as high voltage isolation is required by safety standards such as those set forth above and patient safety is improved.

Figure 3:
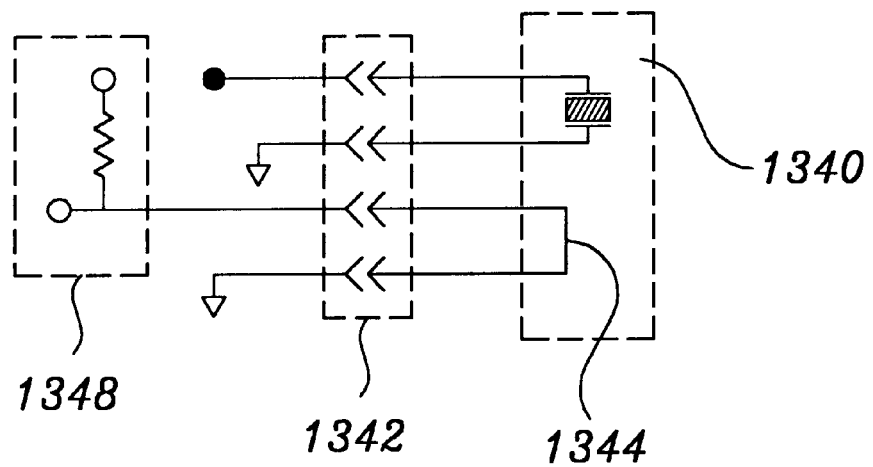
FIG. 3 is an illustration of a prior art circuit to detect the presence of a phacoemulsification handpiece in a grounded patient configuration.
Figure 4:
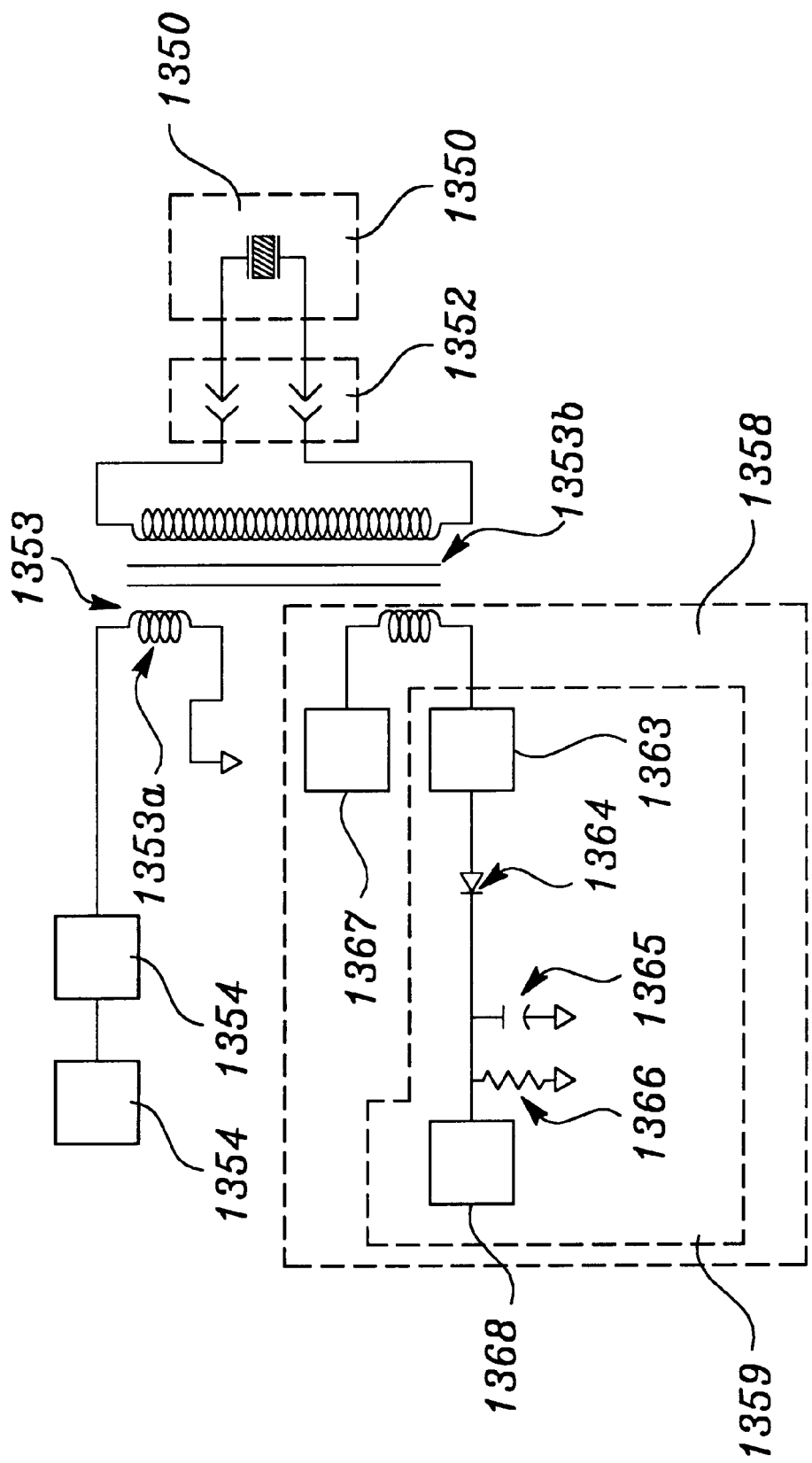
FIG. 4 is an illustration of one embodiment of the isolated phacoemulsification handpiece detection apparatus of the present invention.
Figure 5:
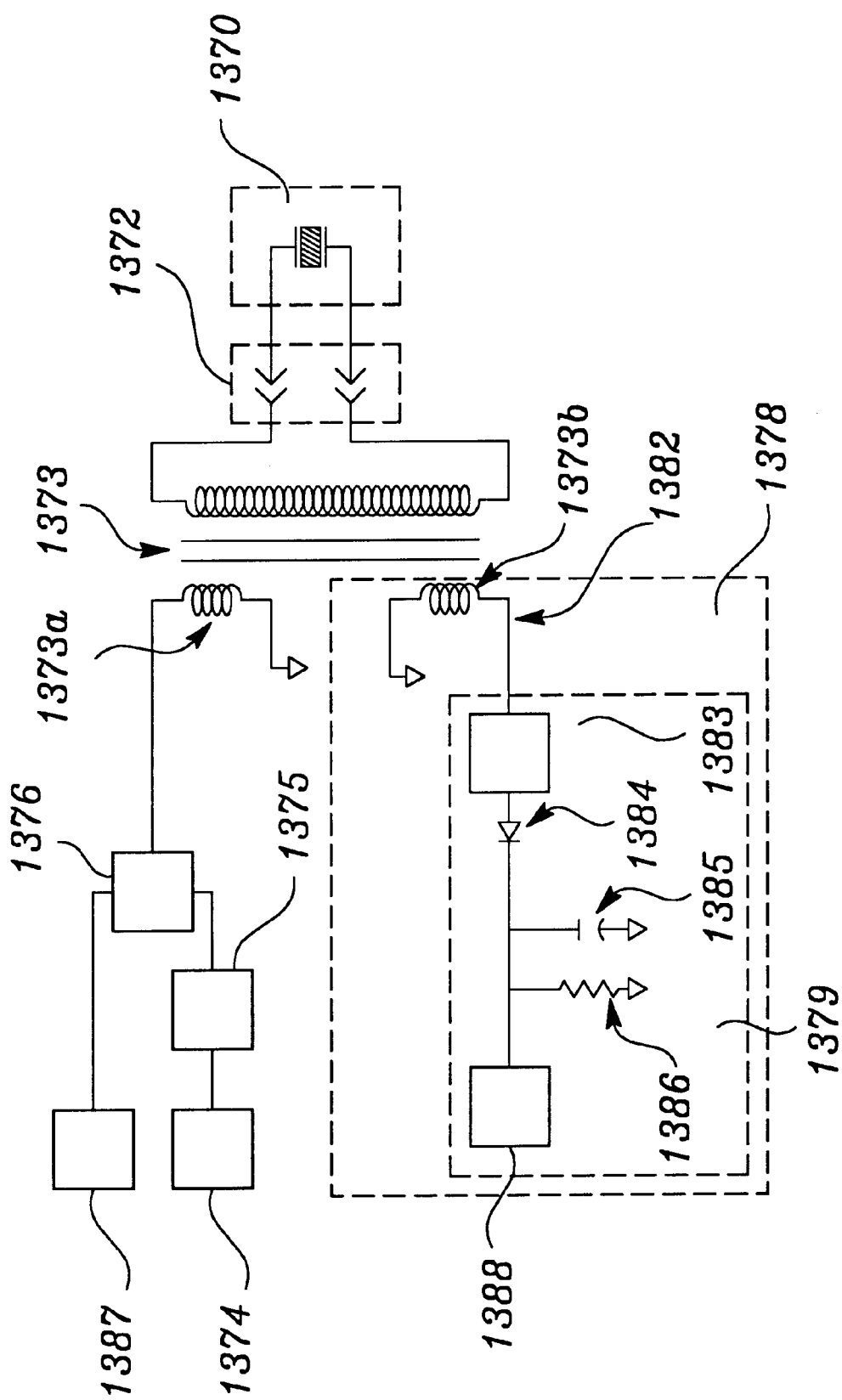
FIG. 5 is an illustration of a second embodiment of the isolated phacoemulsification handpiece detection apparatus of the present invention.

The prior art and another embodiment of the present invention are shown in FIG. 3, FIG. 4 and FIG. 5. FIG. 3 is an illustration of a prior art circuit to detect the presence of a phacoemulsification handpiece in a grounded patient configuration. FIG. 4 is an illustration of one embodiment of the isolated ultrasonic ophthalmic surgical handpiece detection apparatus of the present invention. FIG. 5 is an illustration of a second embodiment of the isolated ultrasonic ophthalmic surgical handpiece detection apparatus of the present invention.

A description of the preferred embodiment is presented in the following paragraphs which describe the prior art shown in FIG. 3 and this embodiment of the invention which is illustrated in FIG. 4 and FIG. 5. Turning to the drawings, FIG. 3 illustrates a prior art circuit to detect the presence of a phacoemulsification handpiece in a grounded patient configuration. The phacoemulsification handpiece or probe 1340 is connected through connector 1342 directly to the electric power source (not shown). The phacoemulsification handpiece 1340 includes shorting bar 1344 which is connected through different connection points in connector 1342 to the detection circuit 1348. When a phacoemulsification handpiece is detected, the control software allows power to be supplied to the handpiece.

FIG. 4 and FIG. 5 illustrate the present invention which has an electrically isolated, floating patient configuration. In FIG. 4 an ultrasonic ophthalmic surgical handpiece or probe 1350 is connected through connector 1352 to the secondary winding of transformer 1353 which provides electric power to the handpiece 1350 while isolating the handpiece 1350 from the electric power source 1354. The handpiece 1350 is a conventionally known probe such as those produced by Storz Instrument Company such as the ultrasonic handpieces used for phacoemulsification and phacofragmentation procedures. Transformer 1353 is a conventional power transformer that provides the desired isolation between the handpiece 1350 and the source of electric power 1354 which is typically an alternating current signal of up to about 30 volts provided at a frequency between 15 k hertz and 35 k hertz. Transformer 1353 has two primary windings, a first primary winding 1353a and a second primary winding 1353b, and one secondary winding. The first primary winding 1353a of transformer 1353 is connected to the electric power source 1354 through apparatus, switch or relay 1355 which is controlled by software activated by a signal from detection apparatus 1358. Relay 1355 may be any conventional electrical or electro-mechanical switch capable of switching the electrical power required by the handpiece 1350 on and off.

Detection apparatus 1358 includes signal source 1367, second primary winding 1353b of transformer 1353 and detection circuit 1359 which is connected to the second primary winding 1353b. Transformer 1353 provides isolation between the handpiece 1350 and the handpiece detection circuit 1359 at the same time that it provides isolation between the handpiece 1350 and the electric power source 1354. End 1362 of the second primary winding 1353b of transformer 1353 is connected through high pass filter 1363 to the anode of diode 1364 (1N918, 1N4148 or similar diode) and resistor 1366 (100 k ohms) and capacitor 1365 (0.01 μfarad) are connected in parallel between the cathode of diode 1364 and ground. Signal source 1367, an alternating current signal source, provides a signal, typically a voltage of approximately 5 volts provided at a frequency substantially higher than the frequency of the signal provided by the electric power source 1354 such as, for example, a frequency between 40 k hertz and 100 k hertz, to the second primary winding 1353b of transformer 1353. Comparator 1368, connected to the cathode of diode 1364, compares the signal that it receives with a standard signal to determine the presence of the handpiece 1350 and, when the handpiece is present, the comparator 1368 provides a signal to the control software which will activate relay 1355 to provide electric power to the ultrasonic ophthalmic surgical handpiece 1350. Alternatively comparator 1368 may be connected directly to relay 1355 so that the output signal from comparator 1368 will activate relay 1355. The detection circuit 1359 detects the presence of the handpiece 1350 by the change in voltage measured.

When relay 1355 is activated, power is applied to the handpiece 1350 through the first primary winding 1353a of transformer 1353. However, the second primary winding 1353b of transformer 1353 will also receive a signal from the power source 1354 through induction from the first primary winding 1353a and the high frequency signal from signal source 1367 will be superimposed upon the lower frequency signal from power source 1354. To prevent overloading detection circuit 1359 with the power signal, high pass filter 1363 will prevent the transmission of the lower frequency power signal to the detection circuit 1359 while allowing the higher frequency, low voltage detection signal from signal source 1367 to pass to the detection circuit 1359.

In operation of the detection apparatus 1358, an alternating current signal, such as a 5 volt, 62.5 k hertz square wave, is provided to the second primary winding 1353b of transformer 1353 by a high impedance signal source 1367. When handpiece 1350 is not connected, the reflected impedance at the second primary winding 1353b of the load from the secondary winding side of transformer 1353 is relatively high and the voltage measured by the detection circuit 1359 connected to second primary winding 1353b is essentially zero. This voltage at the anode of diode 1364 is insufficient to forward bias diode 1364, thus the signal received by comparator 1368 is essentially zero indicating that a handpiece 1350 is not connected. When the handpiece 1350 is connected, the reflected impedance at the second primary winding 1353b of the load from the secondary winding side of transformer 1353 is relatively low, and the voltage measured at the detection circuit 1359 is relatively high. This voltage at the anode of diode 1364 is sufficient to forward bias diode 1364 which rectifies the signal. The rectified voltage signal is then filtered by capacitor 1365 and resistor 1366 before being compared to a standard by comparator 1368. The signal received by the comparator 1368 is relatively high indicating that the handpiece 1350 is connected. When comparator 1368 determines that a handpiece 1350 is present, the comparator 1368 provides a signal to the control software indicating the presence of the handpiece 1350 and the software activates relay 1355, which may be an electric or electromechanical switch, to provide electrical power to the handpiece 1350 through first primary winding 1353a of transformer 1353. When relay 1355 is activated, high pass filter 1363 allows transmission of the high frequency signal from signal source 1367 while blocking the transmission of the lower frequency power signal to prevent damage to the components in detection circuit 1359.

In the operation of the apparatus described above signal source 1367 is a high impedance source. Alternatively signal source 1367 may be a low impedance signal source provided that a resistor is added to detection circuit 1359 between end 1362 of second primary winding 1353b and ground. If a low impedance signal source is used operation of the apparatus will be similar to that described above, but the voltage levels measured will be different.

FIG. 5 illustrates an embodiment of the invention similar to that shown in FIG. 4, however, in FIG. 5 both the electric power from the electric power source and the detection signal from its signal source are applied to the first primary winding of the transformer. In FIG. 5 an ultrasonic ophthalmic surgical handpiece or probe 1370 is connected through connector 1372 to the secondary winding of transformer 1373 which provides electric power to the handpiece 1370 while isolating the handpiece 1370 from the electric power source 1374. The ultrasonic ophthalmic surgical handpiece 1370 is a conventionally known probe such as those produced by Storz Instrument Company such as the ultrasonic handpieces used for phacoemulsification and phacofragmentation procedures. Transformer 1373 is a conventional power transformer that provides the desired electrical isolation between the handpiece 1370 and the source of electric power 1374 which is typically an alternating current signal of up to 30 volts provided at a frequency between 15 k hertz and 35 k hertz. Transformer 1373 has two primary windings, a first primary winding 1373a and a second primary winding 1373b, and one secondary winding. The first primary winding 1373a of transformer 1373 is connected to the electric power source 1374 through apparatus, switch or relay 1375 which is controlled by software activated by a signal from detection apparatus 1378. Relay 1375 may be any conventional electrical or electromechanical switch capable of switching the electrical power required by the handpiece 1370 on and off.

Signal source 1387, a low impedance source, also provides a signal, typically an alternating current signal of approximately 5 volts provided at a frequency substantially higher than the frequency of the signal provided by the electric power source 1374 such as, for example, between 40 k hertz and 100 k hertz, to the first primary winding 1373*a* of transformer 1373 for the handpiece detection apparatus 1378. When a handpiece 1370 is not present, the signal from signal source 1387 is the only signal applied to first primary winding 1373*a*. When a handpiece 1370 is present, the signal from signal source 1387 is superimposed upon the power signal from power source 1374 by summing apparatus 1376 and the superimposed signal is applied to the first primary winding 1373*a* of transformer 1373. The first primary winding 1373*a* is inductively coupled to the second primary winding 1373*b* and the signal applied to the first primary winding 1373*a* produces a corresponding signal in second primary winding 1373*b* which is received by detection circuit 1379.

Detection apparatus 1378 includes second primary winding 1373*b* of transformer 1373 and detection circuit 1379 which is connected to the second primary winding 1373*b*. Transformer 1373 provides isolation between the handpiece 1370 and the handpiece detection circuit 1379 at the same time that it provides isolation between the handpiece 1370 and the electric power source 1374. End 1382 of the second primary winding 1373*b* of transformer 1373 is connected through high pass filter 1383 to the anode of diode 1384 (1N918, 1N4148 or similar diode) and resistor 1386 (100 k ohms) and capacitor 1385 (0.01 μfarad) are connected in parallel between the cathode of diode 1384 and ground. Comparator 1388, connected to the cathode of diode 1384, compares the signal that it receives with a standard signal to determine the presence of the handpiece 1370 and, when the handpiece is present, the comparator 1388 provides a signal to the user interface control software which will activate relay 1375 to provide electric power to the handpiece 1370. Alternatively comparator 1388 may be connected directly to relay 1375 so that the output signal from comparator 1388 will activate relay 1375. The detection circuit 1379 detects the presence of the handpiece 1370 by the change in voltage measured.

When relay 1375 is activated, power is applied to the handpiece 1370 through the first primary winding 1373*a* of transformer 1373. The signal received by first primary winding 1373*a*, the signal from summing apparatus 1376, has the high frequency signal from signal source 1387 superimposed upon the lower frequency power signal from electric power source 1374. The second primary winding 1373*b* of transformer 1373 will continue to receive a signal through induction from the first primary winding 1373*a* and that signal will now correspond to the high frequency signal from signal source 1387 superimposed upon the lower frequency signal from power source 1374. To prevent overloading detection circuit 1379 with the power signal, high pass filter 1383 will prevent the transmission of the lower frequency power signal to the detection circuit 1379 while allowing the higher frequency, low voltage detection signal from signal source 1387 to pass to the detection circuit 1379.

In operation of the detection apparatus 1378, an alternating current signal, such as a 5 volt, 62.5 k hertz square wave, is provided by signal source 1387, a low impedance source, to the first primary winding 1373*a* of transformer 1373 and a corresponding signal is provided by induction at the second primary winding 1373*b*. When the ultrasonic ophthalmic surgical handpiece 1370 is not connected, the first and second primary windings 1373*a* and 1373*b* of transformer 1373 are inductively coupled as a transformer having a 1:1 winding ratio and the signal from signal source 1387 applied at the first primary winding 1373*a* is present at the second primary winding 1373*b*. Thus the voltage measured by the detection circuit 1379 connected to second primary winding 1373*b* is relatively high. The signal from signal source 1387 is allowed to pass by high pass filter 1383. This voltage at the anode of diode 1384 is sufficient to forward bias the diode which rectifies the signal. The rectified signal is filtered by capacitor 1385 and resistor 1386 before being compared to a standard by comparator 1388 which would indicate that the handpiece 1370 is not connected. When the ultrasonic ophthalmic surgical handpiece 1370 is connected, the reflected impedance at the primary windings 1373*a* and 1373*b* of the load from the secondary winding side of transformer 1373 is relatively low, resulting in a lower voltage measured by the detection circuit 1379. High pass filter 1383 allows passage of the high frequency signal to the detection circuit 1379. The lower alternating current voltage at the anode of diode 1384 is insufficient to forward bias diode 1384 and the signal received by comparator 1388 is essentially zero indicating that handpiece 1370 is connected. When the comparator 1388 determines that a handpiece 1370 is present, the comparator 1388 provides a signal to the user interface control software indicating the presence of the handpiece 1370 and the software activates relay 1375, which may be an electric or electro-mechanical switch, to provide electrical power to the handpiece 1370 through first primary winding 1373*a* of transformer 1373. When relay 1375 is activated, the signal received at second primary winding 1373*b* changes to correspond to the high frequency detection signal superimposed upon the power signal provided at first primary winding 1373*a* by summing apparatus 1376. High pass filter 1383 allows transmission of the high frequency signal from signal source 1387 while blocking the transmission of the lower frequency power signal from electric power source 1374 to prevent damage to the components in detection circuit 1379.

It should be recognized that the selected values for the resistors, capacitors and other components and for stated voltages and frequencies are provided for illustration of the invention and not as the only combination and that the values of each may be changed without changing the invention.

The present invention further includes a method for detecting the presence of an ultrasonic ophthalmic surgical handpiece. The method includes the steps of providing an alternating current electric signal to a primary winding of a transformer having a first and a second primary winding and a secondary winding, receiving a second electric signal at the second primary winding determined by the reflected impedance of the load at the secondary winding of the transformer and comparing the second electric signal to a standard to determine the presence of the handpiece. The method may also include the step of activating a switch to connect an electric power source through the first primary winding of the transformer to the detected handpiece.

The electrical isolation provided by the transformer in this invention allows the controls to sense the presence of the handpiece and to provide power to the handpiece while maintaining the integrity of the isolated patient configuration. This is an important safety consideration as high voltage isolation is required by safety standards such as those set forth above and patient safety is improved.

In view of the foregoing, it will be seen that several advantages are attained.

Although the foregoing includes a description of the best mode contemplated for carrying out the invention, various modifications are contemplated.

As various modifications could be made in the constructions herein described and illustrated without departing from the scope of the invention, it is intended that all material contained in the foregoing description or shown in the accompanying drawings should be interpreted as illustrative rather than limiting.

What is claimed is:

1. An apparatus for detecting the presence of an ophthalmic surgical handpiece in an isolated patient configuration comprising and providing power to the surgical handpiece when present:

a transformer having primary and secondary windings;

an alternating current signal source connected to the primary winding of the transformer;

a detection circuit connected to the primary winding of the transformer, the detection circuit comprising a comparator to compare the signal received to a standard signal to determine the presence of the handpiece; and a switch the means to provide power to the handpiece so that power is not delivered to said handpiece;

wherein said comparator sends a signal to said switch to turn the switch to the on position when the handpiece is present to provide power to the handpiece.

2. An apparatus for detecting the presence of an ophthalmic surgical handpiece in an isolated patient configuration comprising:

an isolation transformer having primary and secondary windings;

a surgical handpiece having an ultrasonic transducer and a shorting bar, said shorting bar connected across the secondary winding of the transformer;

an alternating current signal source connected to one end of the primary winding of the transformer; and a detection circuit connected to the end of the primary winding of the transformer opposite the alternating current signal source, the detection circuit comprising a comparator to compare the signal received to a standard signal to determine the presence of the ophthalmic surgical handpiece.

3. A method for detecting the presence of an ophthalmic surgical handpiece in an isolated patient configuration and providing power to the surgical handpiece when present comprising:

providing an alternating current electric signal to the primary winding of a transformer;

receiving a second electric signal determined by the reflected impedance of the load on the secondary winding of the transformer;

comparing the second reflected signal to a standard to determine the presence of the ophthalmic surgical handpiece;

sending a third signal to an initially off on-off power switch when the presence of the surgical handpiece is detected to move the power switch to the on position to provide power to the surgical handpiece.

4. The method of claim 3 further comprising the step of activating a switch when an ophthalmic surgical handpiece is detected to connect an electric power source to the ophthalmic surgical handpiece.

* * * * *